United States Patent
Glenn et al.

(10) Patent No.: US 10,748,439 B1
(45) Date of Patent: Aug. 18, 2020

(54) AUTOMATED DELIVERY OF UNIQUE, EQUIVALENT TASK VERSIONS FOR COMPUTER DELIVERED TESTING ENVIRONMENTS

(71) Applicant: The Cognitive Healthcare Company, San Francisco, CA (US)

(72) Inventors: Shenly Glenn, San Francisco, CA (US); Joel Mefford, Benicia, CA (US)

(73) Assignee: THE COGNITIVE HEALTHCARE COMPANY, Mountain View, CA (US)

( * ) Notice: Subject to any disclaimer, the term of this patent is extended or adjusted under 35 U.S.C. 154(b) by 553 days.

(21) Appl. No.: 14/882,378

(22) Filed: Oct. 13, 2015

Related U.S. Application Data

(60) Provisional application No. 62/062,993, filed on Oct. 13, 2014.

(51) Int. Cl.
| | | |
|---|---|---|
| *G09B 7/00* | (2006.01) | |
| *A61B 5/00* | (2006.01) | |
| *G09B 7/02* | (2006.01) | |
| *A61N 1/36* | (2006.01) | |
| *A61B 5/0484* | (2006.01) | |
| *A61B 5/16* | (2006.01) | |

(52) U.S. Cl.
CPC .............. *G09B 7/00* (2013.01); *A61B 5/4088* (2013.01); *G09B 7/02* (2013.01); *A61B 5/0484* (2013.01); *A61B 5/16* (2013.01); *A61B 5/162* (2013.01); *A61B 5/168* (2013.01); *A61B 5/4064* (2013.01); *A61B 5/4082* (2013.01); *A61B 5/486* (2013.01); *A61N 1/36082* (2013.01); *A61N 1/36103* (2013.01)

(58) Field of Classification Search
CPC ........ G09B 7/00; G09B 7/02; A61N 1/36082; A61N 1/36103; A61B 5/4088; A61B 5/16; A61B 5/162; A61B 5/0484; A61B 5/4082; A61B 5/168; A61B 5/486; A61B 5/4064
USPC .......................................................... 434/322
See application file for complete search history.

(56) References Cited

U.S. PATENT DOCUMENTS

| | | | |
|---|---|---|---|
| 5,956,671 A | 9/1999 | Ittycheriah et al. | |
| 8,083,353 B2 * | 12/2011 | Hytowitz | A61B 3/032 351/239 |
| 8,165,407 B1 * | 4/2012 | Khosla | G06K 9/4623 382/164 |
| 8,606,581 B1 | 12/2013 | Quast et al. | |
| 8,781,831 B2 | 7/2014 | Ljolje et al. | |
| 8,821,242 B2 * | 9/2014 | Hinman | A63F 13/10 463/15 |

(Continued)

*Primary Examiner* — Jack Yip
(74) *Attorney, Agent, or Firm* — Redbrick IP, P.C.

(57) ABSTRACT

A client device is configured to administer unique, equivalent, computer mediated, task versions of a particular task type automatically generated by a task versioning system. Multiple task versions, each comprising of at one stimulus sequence, are generated by performing geometric, symmetric or temporal transformations on the spatiotemporal relationships between one or more stimuli in a task version. Previous user performance may be captured and analyzed to determine a next task version. Task versioning systems with the ability to automatically generate multiple unique, equivalent task versions allow for accurate measurement of neurological, cognitive, and motor skills, by ensuring that learning effects arising from repeated task administrations are eliminated.

16 Claims, 11 Drawing Sheets

(56) References Cited

U.S. PATENT DOCUMENTS

| | | | |
|---|---|---|---|
| 8,830,189 B2 | 9/2014 | Rimon et al. | |
| 8,856,543 B2 | 10/2014 | Geiger et al. | |
| 8,866,752 B2 | 10/2014 | Westerman et al. | |
| 9,063,647 B2 | 6/2015 | Zotov et al. | |
| 9,075,462 B2 | 7/2015 | Sauer et al. | |
| 9,092,125 B2 | 7/2015 | Michaelis et al. | |
| 9,141,284 B2 | 9/2015 | Sands et al. | |
| 9,147,059 B2 | 9/2015 | Isbister et al. | |
| 9,237,842 B2* | 1/2016 | Lee | A61B 3/036 |
| 9,302,179 B1* | 4/2016 | Merzenich | A63F 13/80 |
| 2005/0080592 A1 | 4/2005 | Buscema et al. | |
| 2006/0132283 A1 | 6/2006 | Eberhart et al. | |
| 2007/0166675 A1* | 7/2007 | Atkins | G09B 5/06 |
| | | | 434/236 |
| 2007/0265507 A1* | 11/2007 | de Lemos | A61B 3/113 |
| | | | 600/300 |
| 2007/0298385 A1* | 12/2007 | Jenkins | G09B 5/06 |
| | | | 434/156 |
| 2009/0130640 A1* | 5/2009 | Hardy | G09B 19/00 |
| | | | 434/236 |
| 2011/0066082 A1* | 3/2011 | Duffy | A61B 5/1113 |
| | | | 600/595 |
| 2012/0030570 A1 | 2/2012 | Migos et al. | |
| 2012/0330178 A1 | 12/2012 | Kraft et al. | |
| 2012/0330182 A1* | 12/2012 | Alberts | G09B 23/28 |
| | | | 600/558 |
| 2013/0216986 A1* | 8/2013 | Goldman | G09B 19/00 |
| | | | 434/236 |
| 2014/0026212 A1 | 10/2014 | Geiger et al. | |
| 2014/0336539 A1 | 11/2014 | Torres et al. | |
| 2015/0213244 A1 | 7/2015 | Lymberopoulos et al. | |
| 2015/0242812 A1 | 8/2015 | Nelson et al. | |
| 2016/0089017 A1* | 3/2016 | Wang | A61B 3/0091 |
| | | | 351/239 |
| 2016/0100788 A1* | 4/2016 | Sano | A61B 5/121 |
| | | | 600/595 |
| 2016/0034738 A1 | 10/2016 | Luo | |
| 2016/0063236 A1 | 12/2016 | Masuko | |
| 2016/0357429 A1 | 12/2016 | Nilo et al. | |

* cited by examiner

| Order (420) | Sequence 1 (440A) | Sequence 2 (440B) | Sequence 3 (440C) | Sequence 4 (440D) |
|---|---|---|---|---|
| 1 | 0.5 (460) | 0.5 | 1 | 0.75 |
| 2 | 0.5 | 0.5 | 0.5 | 1 |
| 3 | 1 | 0.5 | 0.5 | 0.5 |
| 4 | 1 | 1 | 0.5 | 0.5 |
| 5 | 1 | 1 | 1 | 0.5 |
| 6 | 0.75 | 1 | 1 | 1 |
| 7 | 0.75 | 0.75 | 1 | 1 |
| 8 | 1 | 0.75 | 0.75 | 1 |
| 9 | 0.5 (480) | 1 | 0.75 | 0.75 |

FIG. 4C

| Order | Sequence 1 | Sequence 2 | Sequence 3 | Sequence 4 |
|---|---|---|---|---|
| 1 | L0.5 | L0.5 | L1 | R0.75 |
| 2 | L0.5 | R0.5 | R0.5 | L1 |
| 3 | L1 | R0.5 | L0.5 | R0.5 |
| 4 | R1 | R1 | L0.5 | L0.5 |
| 5 | L1 | L1 | L1 | L0.5 |
| 6 | R0.75 | R1 | R1 | L1 |
| 7 | R0.75 | L0.75 | L1 | R1 |
| 8 | L1 | L0.75 | R0.75 | L1 |
| 9 | R0.5 | R1 | R0.75 | R0.75 |

FIG. 5E

AUTOMATED DELIVERY OF UNIQUE, EQUIVALENT TASK VERSIONS FOR COMPUTER DELIVERED TESTING ENVIRONMENTS

CROSS-REFERENCE TO RELATED APPLICATION

This application claims priority under 35 U.S.C. § 119(e) to U.S. Provisional Patent Application Ser. No. 62/062,993, "Method and system for the automated delivery of unique, equivalent task versions upon repeated administration and the collection of equivalent variables across unique, equivalent task versions to limit learning effects and ensure limited variability of results upon repeat administration of task," filed Oct. 13, 2014, which is incorporated herein by reference in its entirety.

TECHNICAL FIELD

The disclosed embodiments generally relate to generating repeated task versions of computer mediated tasks in computer based testing systems that reduce learning effects on the test takers. In particular, the disclosed embodiments relate to the automatic generation of equivalent task versions for computer tests measuring cognitive, motor, and other neurologically related functions in order to reduce the numbers of subjects needed to validate same-task versions.

BACKGROUND

In the field of neurological and neuropsychological testing, subjects are presented with various diagnostic tests that are designed to measure cognitive and motor performance. Typically tests comprise tasks manipulating of concrete objects such as blocks or puzzle pieces, joy sticks, steering wheels, pedals, levers, styluses or other implements to test motor skills, or memorization of lists or sequences to test cognitive skills, or a combination thereof. The tests are often timed, and the subject's performance is scored or otherwise evaluated by a clinician observing the test where each neurological or neuropsychological test may be referred to as a task. To measure a subject's potential changes in motor or cognitive skills over time, it would be useful to re-administer tests periodically. However, it is generally accepted that repeated administration results in learning effects; the minimum recommended time to repetition ranges from 3-12 months, depending on the memory status of the subject being tested, and even then, learning effects are considered to be problematic. That is, repetition of a test allows a subject to learn test mechanisms and test stimuli, so that the test no longer measures its intended cognitive domain, but rather, memory, and subjects can improve the performance with each repetition. As a result, this improved performance may mask actual deterioration of cognitive or motor skills, and thereby delay appropriate diagnosis of neurological problems.

SUMMARY

A computerized task versioning system (TV S) is configured to generate multiple equivalent versions of computer generated task types of a particular computer mediated test (task) of cognitive, motor, and other measurable skills. Each non-equivalent computer mediated neurological test is considered a unique test type (task type). Providing multiple equivalent versions of computer mediated task types (task versions) for different task types beneficially improves accurate measurement of potential changes in user's skills by eliminating the effects of user's learning tasks through repeated test administration. Thus, the TVS is configured to more accurately identify changes in user's skills over time, resulting in improved identification and diagnosis of neurological impairments.

The TVS presents various task versions associated with a task type via the user's client device. Each task version comprises one or more stimuli wherein each stimulus may be embedded with one or more alpha-numeric symbols that are control-randomly generated to ensure the creation of unique, equivalent task versions. Additionally, task versions are defined by the spatiotemporal relationships between their constituent stimuli. The user responds to symbols (letters, words, numbers, etc.) associated with stimuli with inputs such as touches, tapping, dragging, or other physical interactions. The TVS monitors each user's completion of the presented task versions associated with a given task type and provides new task versions to the user during repeat test administrations based on a measure of the user's prior performance. These new task versions may be dynamically generated as or after each test is complete. In another embodiment, new task versions may be generated a priori, and stored for subsequent selection and retrieval.

Each version of a task type (the associated task version) is generated and evaluated using intra and inter sequence rules. These intra and inter sequence rules select stimuli for the task type in a manner that renders the generated task versions equivalent in terms of length and complexity but sufficiently different (unique) so as to eliminate, to a statistically significant degree, the impact of task version learning or memorization on the user's performance arising from repeat task administration. A new task version can be generated from sequences of stimuli comprising alpha-numeric symbols for display based on rules governing the allowed symmetric, spatiotemporal sequence relationships. For example, the TVS tracks previously administered sequences of stimuli to ensure non-duplication of task versions and a conformance to the intra and inter sequence rules. The user's performance data may be recorded, persisted and referenced for subsequent trials.

In one or more embodiments, the TVS may create unique, equivalent task versions by performing graphical transformations on spatial relationships between one or more stimuli in a previously presented task version. These graphical transformations may include cyclic permutations on spatiotemporal relationships between one or more adjacent stimuli such as positional shifting, cycling of symmetric properties or any combination thereof. For example, in some embodiments, the sequence of stimuli presentation may be cycled to produce unique equivalent task versions. Cycling involves starting the sequence at different points in the sequence for each version. For example, a sequence may be cycled by presenting the sequence from the position of the first stimulus, then in the next version starting the sequence at the second stimulus, placing the first stimulus last, and then in the version starting at the third stimulus, and presenting the first and second stimulus last, and so forth for each subsequent version. A more general embodiment for cycling a sequence of M stimuli involves presenting each of the Nth next stimuli, where N and M are relatively prime. For example for a sequence of M=10 items, N may be 3, and the first task version presents the sequence starting with the first stimulus, the second task version may start at the fourth stimulus, the third task version may start at the seventh stimulus and so forth. In other embodiments, task versions may be generated by transformations including one or more rotations, reflections, angular shifts, positional shifts or any combination thereof.

In other embodiments, inter-stimulus presentation time intervals, stimulus spatial locations or any combination of spatiotemporal relationships may be cycled in order to produce equivalent, unique task versions. Cycling inter-stimulus presentation time intervals maintains the sequence beginning and end, but cycles the intervals between the stimuli. Cycling spatiotemporal relationships cycles linear or angular distances between the stimuli. In still other embodiments, cyclic permutations of inter-stimulus spatiotemporal relationships may be combined with geometric transformations of the symmetric properties of stimuli to allow for variations in inter and intra stimuli relationships that may not otherwise result from the spatiotemporal cyclic permutations alone. For example, a stimulus may also be rotated or reflected across a local plane to produce equivalent variations between task versions.

The TVS may track the previous spatiotemporal relationship of each presented stimuli to the user to ensure the presentation of unique, equivalent task versions at the client device of the user. In still other embodiments, the TVS tracks the sidedness of each stimulus during rotation and reflection operations (e.g., left or right sided stimuli) to allow the preservation of the ratio and number of stimuli presented, while altering stimuli appearance to control for learning effects.

In some implementations, the TVS may produce different, equivalent unique task versions by maintaining the relative angles and distances between stimuli. In one or more embodiments, as the measured user performance on a particular task version increases, additional task versions may be produced with increasing complexity or duration, for example with an increasing number of stimuli displayed on the client device during a given version. Similarly, as the measured user performance decreases, the number of stimuli may decrease or terminate the test. In some embodiments, different task versions may be created in which prior user performance is used to determine inter-stimuli spatiotemporal relationships. For example, task versions may be based on prior user performance. Furthermore, user performance on previously presented task versions may be used to specify the angle and distance between the displayed stimuli in addition to other stimuli spatiotemporal relationships.

The TVS provides improvements in the generation of tests for cognitive and motor skills, including improvements in the accuracy and reliability of such tests to identify neurophysiological, cognitive, motor and other types of testable deficits.

All of the aforementioned embodiments and implementations of the TVS may be implemented on a client device or an external server.

The features and advantages described in this summary and the following detailed description are not all-inclusive. Many additional features and advantages will be apparent to one of ordinary skill in the art in view of the drawings, specification, and claims hereof.

BRIEF DESCRIPTION OF THE DRAWINGS

FIGS. 4A-4C illustrate positional and temporal cyclic permutations in accordance with one embodiment.

FIGS. 5A-5E illustrate cyclic permutations of stimulus spatial locations with implemented geometric transformations of stimuli symmetric properties while preserving angle and distance relationships in accordance with one embodiment.

The figures depict various embodiments of the present invention for purposes of illustration only. One skilled in the art will readily recognize from the following description that other alternative embodiments of the structures and methods illustrated herein may be employed without departing from the principles of the invention described herein.

DETAILED DESCRIPTION

System Overview

Figure 1:
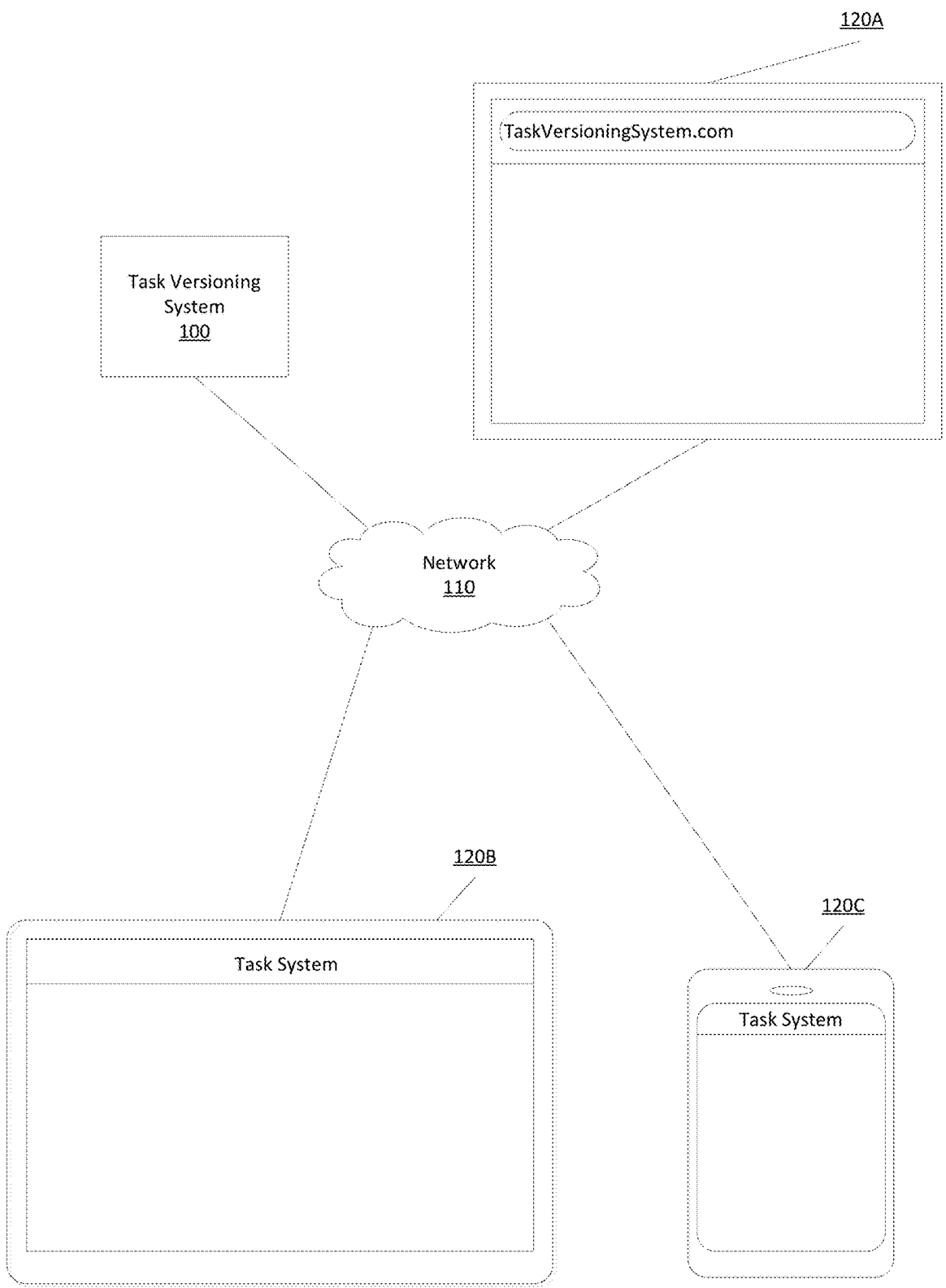
FIG. 1 shows a diagram of a system environment of a task versioning system according to one embodiment.

FIG. 1 shows a system environment including TVS 100, network 110 and client devices 120A, 120B, 120C (collectively or individually "120"). Client devices 120 present, via execution of one or more computer programs, tasks for a user to complete by inputting commands to the client device 120. Client device 120A is a web-based client application. Client 120B is a tablet device running a local client application of the TVS 100. Client device 120C is a smartphone device also running a client application. The TVS 100 provides program data to the client devices which describe the task versions and is one means for providing this function. A client device 120 receives the task version data, and uses it to configure and present the specific version of the task to the user.

The network 110 represents the communication pathway between the TVS 100 and the client device 120, and is one means of connecting the two devices. In one embodiment, the network 110 uses standard wireless and wired communications technologies and protocols and can include the Internet and associated protocols. In another embodiment, the entities on the network 110 can use custom and/or dedicated data communications technologies.

Client Device

Figure 2:
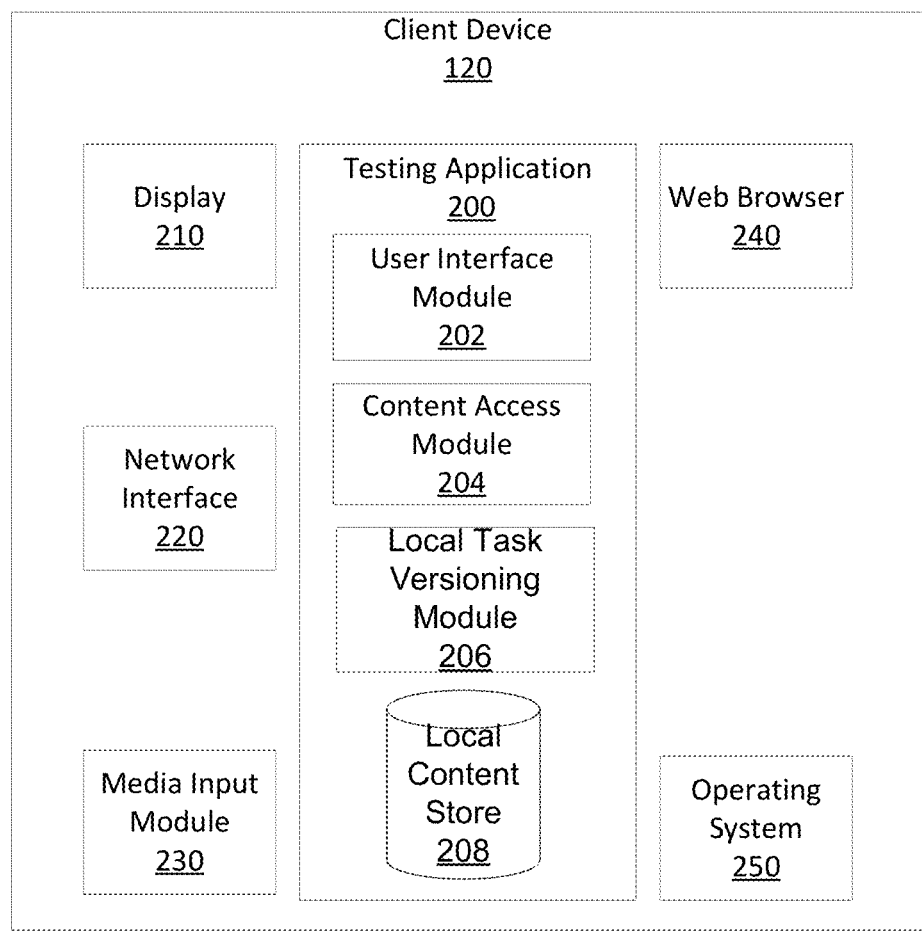
FIG. 2 shows a block diagram of the components of a client device.

FIG. 2 shows a block diagram of the components of a client device 120 according to one embodiment. A client device 120 generally comprises devices and modules for communicating with TVS 100 and a user of client device 120 and is one means for providing this function. Client device 120 includes a client testing application 200 for presenting task versions based on the task version data transmitted by TVS 100. The testing application 200 includes user interface module 202, content access module 204, local task versioning module 206 and local content store 208. The client device 120 also contains a display 210 for providing information to the user, and in certain client devices 120 includes a touchscreen. Additionally, client device 120 also includes network interface 220 for communicating with TVS 100 via network 110, a media input module 230, a web browser 240 web browser 240, an operating system 250. Other components of a client device 120 that are not material are not shown, for example, one or more computer processors, local fixed memory (RAM and ROM), as well as optionally removable memory (e.g., SD-card), power sources, and audio-video outputs.

Client devices 120 maintain various types of components and modules for operating the client device and accessing TVS 100. The software modules include operating system 250. Operating system 250 on each device provides a local file management system and executes the various software modules such as the testing application 200. The testing application 200 and its modules are not part of the native software (including operating system 250) of the underlying client device 120, but provide functionality that extends beyond the generic functions of the client device 120.

Client devices 120 may communicate with TVS 100 through network 110. The network may be any suitable communications network for data transmission. In one embodiment, network 110 is the Internet and uses standard communications technologies and/or protocols. Thus, network 110 can include links using technologies such as Ethernet, 802.11, worldwide interoperability for microwave access (WiMAX), 3G, digital subscriber line (DSL), asynchronous transfer mode (ATM), InfiniBand, PCI Express Advanced Switching, etc. Similarly, the networking protocols used on network 110 can include multiprotocol label switching (MPLS), the transmission control protocol/Internet protocol (TCP/IP), the User Datagram Protocol (UDP), the hypertext transport protocol (HTTP), the simple mail transfer protocol (SMTP), the file transfer protocol (FTP), etc. The data exchanged over network 110 can be represented using technologies and/or formats including the hypertext markup language (HTML), the extensible markup language (XML), etc. In addition, all or some of links can be encrypted using conventional encryption technologies such as the secure sockets layer (SSL), transport layer security (TLS), virtual private networks (VPNs), Internet Protocol security (IPsec), etc. In another embodiment, the entities use custom and/or dedicated data communications technologies instead of, or in addition to, the ones described above.

Client devices 120 communicate with TVS 100 in a variety of ways. Client device 120 may access the TVS 100 using a custom software module, such as testing application 200. Client device 120 may also access TVS 100 through web browser 240 which is one means for providing this function (as further configured by client side coding such as Java). Testing application 200 includes user interface module 202 that generates an interface for a each type of task, given the task version data. In one or more embodiments, a task version may be generated by TVS 100 and provided to testing application 200 over the network 110 for display through content access module 204. Alternatively, in some embodiments, the testing application 200 can generate task versions locally through the local task versioning module 206 which is one means for generating task versions locally. The local task versioning module 206 may generate task versions by receiving a set of task types, task version, task versioning rules and user performance from the local content store 208 (further described below). The generated task version is then presented to the user by the display 210.

In some embodiments, the testing application 200 may locally store content in local content store 208 and is one means for providing this function. This stored content may include a predetermined set of task types and task versions, a set of task types and task versions previously completed by a user, a measure of user performance, and a set of one or more predefined task versioning rules provided by TVS 100. While represented here as within testing application 200, local content store 208 may be stored with other data for client device 120 in non-volatile storage.

In certain embodiments, client device 120 includes additional components such as media input module (MIM) 230. MIM 230 may comprise a camera, a microphone or other device designed to provide user input. MIM 230 may be used by testing application 200 to increase the variety of the task variants and one means for obtaining audio, visual in addition to tactile feedback.

Task Versioning System

Figure 3:
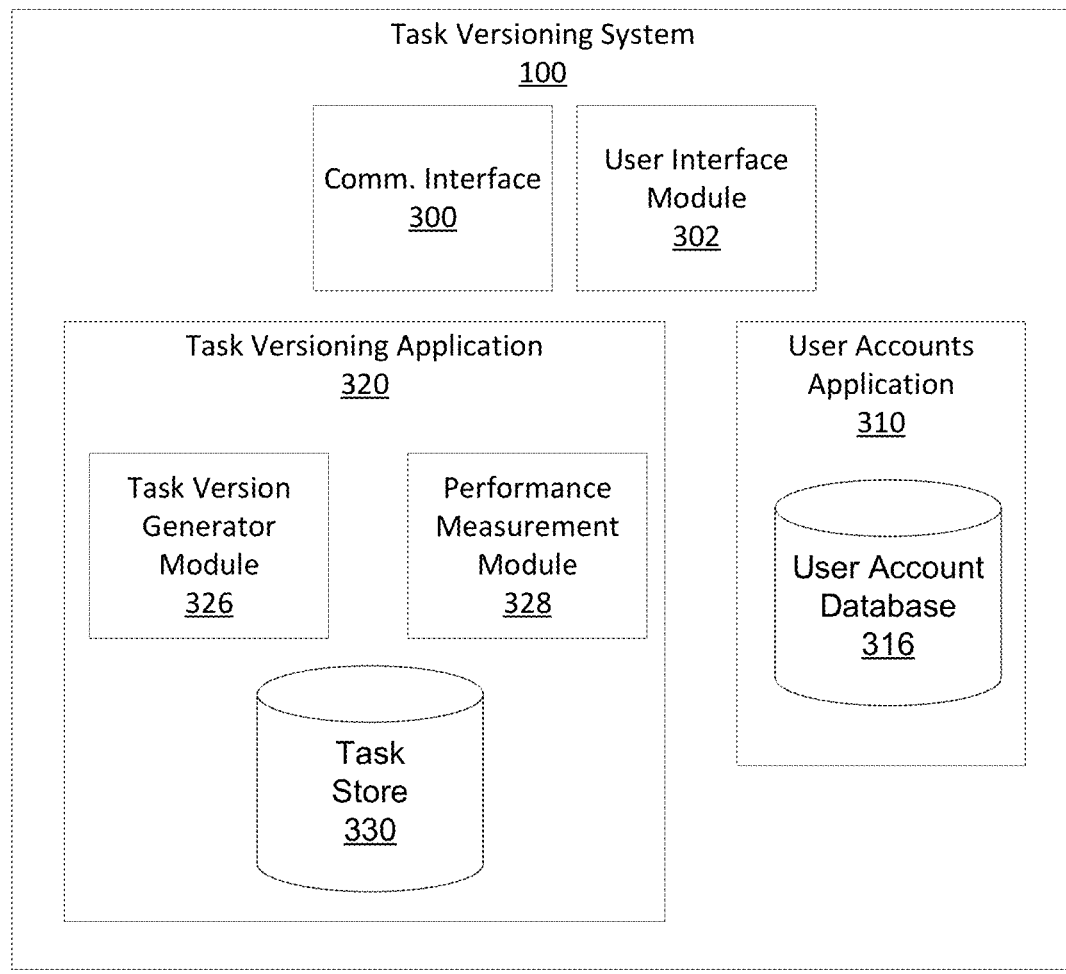
FIG. 3 shows a block diagram of task versioning system.

FIG. 3 shows a block diagram of the TVS 100 according to one embodiment. TVS 100 includes communication interface 300 to enable communication with client devices 120, a user interface module 302, a task versioning application 320 and a user accounts application 310.

TVS 100 includes communications interface 300 for interfacing with various client devices 120, and with other content and/or service providers via an Application Programming Interface (API), which is one means for performing this function. Certain software applications may access a set predetermined task types, generated task versions, completed task versions and measured performance through the task versioning application 320 via an API on behalf of a user. For example, a software package, such as an app on a smartphone or tablet computing device, can programmatically make calls directly to TVS 100, when a user provides credentials, to read, write, create, delete, or otherwise manipulate content. Similarly, the API can allow users to access all or part of content storage 318 through a website.

TVS 100 may also enable the user to view or manipulate content via the user interface module 302 which is one means for providing this function. For example, the user can navigate to the TVS 100 using a web browser 260 to a web address provided by TVS 100 via the client device 120. Moreover, n one or more embodiments, the user may make changes or updates to content in user account database 315, task store 330 or any combination thereof through a web interface provided by the user interface module 302. Updates or changes may include completing a task version or obtaining a new performance score associated with the user's account. Multiple client devices 120 may be associated with a single account and files in the account.

To facilitate the various task versioning services, in some embodiments, a user may create an account with TVS 100 using the user accounts application 310. The user accounts application 310 is one means for storing user provided information in user account database 316. For example, user account database 316 can store profile information including completed tasks, task versions and measured performance for registered users. In some cases, the only personal information in the user profile can be a username and/or email address. However, TVS 100 can also be configured to accept additional user information. This additional user information may include password recovery information, demographics information, and other details.

Each user is associated with a userID and a user name. For purposes of convenience, references herein to information such as task versions, task types, user performance or other data being "associated" with a user are understood to mean an association in database such as task store 330, user account database 316. Similarly between a task version, task type and/or prior performance and either of the above forms of user identifier for the user. Performance processing operations on user performance measurements are understood to be operations performed on corresponding identifiers such as taskID, taskversionID and userIDs. For example, a user may be associated with a task version by storing the information linking the userID, the taskID and taskversionID in a table, file, or other storage formats in. For example, a database table organized by taskversionIDs can include a column listing the userID of each user who has completed that specific task version. As another example, for each userID, a file can list a set of taskversionIDs for the tasks completed by the user. A single file can list key value pairs such as <userID, taskID, taskversionID, performance> representing the association between an individual user and a task including the task version and measured user performance.

Task Version Generation

TVS 100 may automatically generate, manage, store and share task versions including task results across one or more client devices 320. Additionally, TVS 100 may share with the user accounts database 316 the completed tasks, task versions and measured user performance. In one or more embodiments, the task versioning application 320 may comprise a task version generator module 326, a performance measurement module 328 and a task store 330. The TVS 100 and its modules are not native components of the underlying computer(s) on which the TVS 100 executes, but rather extend the functionality beyond the generic functions of such computer(s) in the manner described herein.

Various task types associated with a user may be stored in task store 330 which is one means for performing this function. Task Store 330 can be a storage device, multiple storage devices, or a server. Alternatively, task store 330 can be stored on a cloud storage provider or a network storage location accessible via one or more communications networks. In one embodiment, task types stored in task store 330 are characterized by the presentation of one or more stimuli sequences. Each stimulus within the stimuli sequence may be characterized by an alphanumeric symbol (e.g., "1", or "A"), a presentation location on the user device 120 (base location), sequence order and graphical features (e.g., shapes, colors, textures). In other embodiments, stimuli may comprise one or more audio recordings comprising spoken dialog or instructions wherein the user must respond verbally. In an embodiment, controlled-random stimuli are presented to ensure equivalent levels of difficulty across different task versions associated with a given task type.

In addition to storing task types, in one or more embodiments, task store 330 may also store predetermined interaction rules governing the method and type of user interaction required. For example, some predetermined interaction rules associated with one or more task types may require the user to select stimuli in a particular order. Interaction rules associated with one or more task types may require other audiovisual or tactile feedback from the user. In other embodiments, task store 330 may also store previously generated task versions associated with particular task type in task store 330.

The task versioning application 320 also includes a task version generator module 326 which is one means for generating unique, equivalent task versions associated with a particular task type, and is one means for performing this function. Task versions generated by the task version generator module 326 may be generated dynamically or a priori based on a set of predetermined presentation rules wherein the rules used are associated with each unique task type stored in task store 330. In some embodiments, the set of predetermined presentation rules may govern relationships between the stimuli, in terms of the number of stimuli repetitions in a given stimuli sequence, the types of alphanumeric characters associated with a stimulus in a given stimuli sequence, the degree of randomness in a stimuli sequence or any combination thereof. Presentation rules are further described, below, in conjunction with FIG. 4.

In one or more embodiments, task version generator module 326 may communicate with user account database 316 and/or task store 330. Previously presented task versions and measured performance associated with a particular user may be obtained through the user account database 316. On the other hand, task types and the associated predetermined interaction and presentation rules may be obtained from the task store 330. Through the application of the rules associated mentioned above, the task version generator module ensures the generation of unique, equivalent task versions associated with a task type. Examples of presentation rules, interaction rules or any combination thereof are described further in conjunction with FIGS. 4, 5 and 6.

In one or more embodiments, the task version generator module 326, generate a task version by performing a plurality of transformations comprising one or more temporal, spatial, symmetric or any combination thereof cyclic permutations on the presentation order of a stimuli sequence associated with a previously generated task version. The aforementioned transformations are performed such that upon repeated presentation of the same task type, unique equivalent task versions may be generated by cycling the starting point (e.g., presentation order, rotational and reflection state, position) of each previously presented stimuli series.

In one embodiment, a task version such as a stimuli sequence comprising a first stimulus and a second stimulus are spatially cycled by task version generator module 326 such that in a subsequent stimuli sequence, the first stimulus is presented in place of the second stimulus while the second stimulus is presented in place of the first. In a more general embodiment of spatiotemporal cycling, a sequence of M stimuli is presented wherein the Nth next stimulus is chosen to be presented first in the next task version presented, where N and M are relatively prime. For example for a sequence of M=10 stimuli, N may be 3, and the first task version presents the sequence starting with the first stimulus, the second task version may start at the fourth stimulus, the third task version may start at the seventh stimulus and so forth. Doing so allows the task versioning application 326 to preserve the distance and angles between different stimuli and the time to completion. Spatiotemporal cycling is further described in conjunction with FIG. 4.

In other embodiments, unique equivalent task versions may be obtained by cycling symmetric properties (e.g., rotations, reflections, etc.) of individual stimuli within a stimuli sequence, sequence of stimuli or combination thereof. For example, a first task version comprising of a first stimulus wherein a second task version is generated by reflecting or rotating the first stimulus with respect to its orientation in the first task sequence. In another embodiment, a second task version comprising a sequence of stimuli may be generated by rotating or reflecting a sequence of stimuli with respect to that present in the first task version. In still other embodiments, cyclic permutations of symmetric properties may be combined with cyclic permutations of spatiotemporal relationships to account for permutations of positional details that may not otherwise be affected by cyclic permutations of spatial relationships alone. This is further described below in conjunction with FIG. 5.

The task version generator 326 may also be configured to track prior user performance obtained from the performance measurement module 328 and is one means for providing this function. In this way, the task version generator 326 may determine the number of stimuli to be presented in accordance with a particular task based on a measure of prior user performance. A measure of task performance may be the time required, by the user, to complete a task, accuracy of received user feedback, some audio visual input provided by the user or any combination thereof. For example, interaction rules associated with one or more task types may require other verbal or tactile responses from the user. In the case of verbal responses, the user speaks a response (e.g., repeating a list of words, numbers, letters, or naming objects displayed), and this verbal response is recorded by the client device, and then processed using speech recognition algorithms (e.g., as disclosed in U.S. Pat. Nos. 5,956,671, 8,606,581, or 8,781,831 to identify the content of the response. The content is then compared with the predetermined responses to determine whether the user accurately completed the task.

Figure 4A:
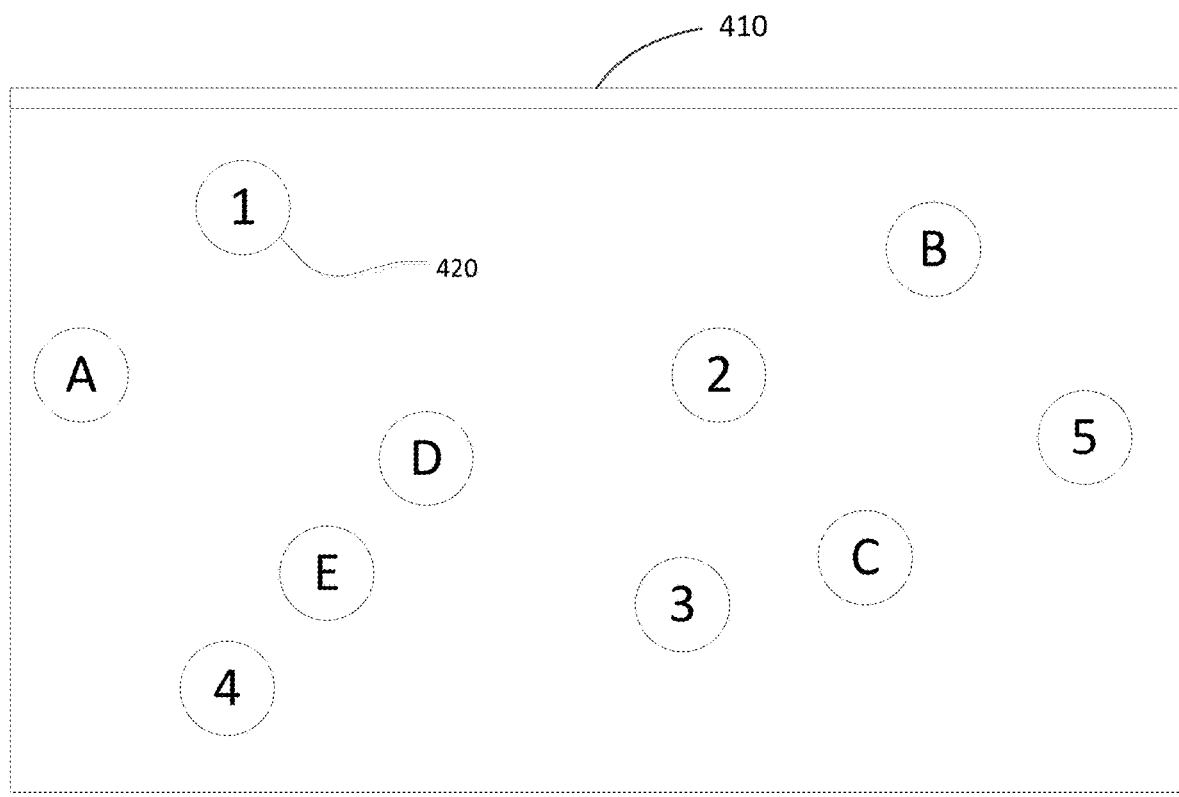

FIG. 4 illustrates a client device 120 displaying a first task version 410 and a second task version 430 generated by TVS 100 in accordance with an embodiment. The task versions 410 and 430 generated by task version generator module 326 comprise a controlled-randomly generated sequence of stimuli arranged in a fixed position on the display of client device 120. Each stimuli sequence, comprising multiple stimuli characterized by alphanumeric symbols 420. FIG. 4A shows a first task version 410 comprising multiple alphanumeric stimuli 420 presented to a user on a client device 120. The task version 410 is presented in a user interface window generated by client device 120 for presentation to the user, along with an interface to capture user inputs to the window (such as touches, drags, keystrokes, and the like).

The task type shown in FIG. 4A requires the user to touch the stimuli 420 in alternating numeric and alphabetical order, e.g., touching the stimuli in the sequence (1, A, 2, B, 3, C, 4, D, 5, E, 1). If this task type were presented to the user multiple times, they would soon learn the relative position of each stimulus on the client device 120 and would thereby improve their performance in terms of time and accuracy.

Figure 4B:
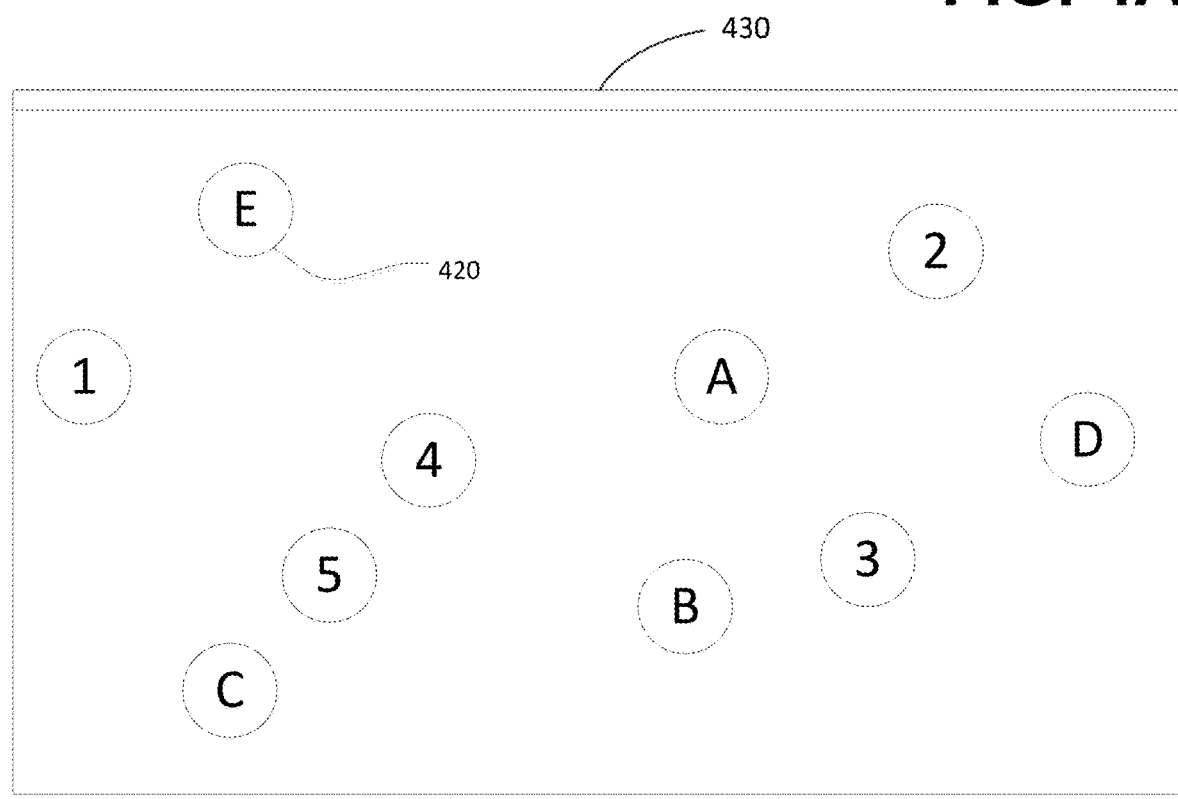

FIG. 4B illustrates a second task version 430 generated by a transformation comprising a spatial permutation of task version 410 in accordance with an embodiment. Examination of FIGS. 4A and 4B shows that stimulus 1 has shifted to the position of stimulus A, stimulus A has shifted to the position of stimulus 2, stimulus 2 has shifted to the position of stimulus B, stimulus B has shifted to the position of stimulus 3, and so forth, completing with stimulus E shifting to the position of stimulus 1. Thus, task version 430 is unique but equivalent to task version 420 since the spatial relationships between adjacent stimuli in the sequence are maintained. The shifts here are not limited to only the location of the immediately following stimulus; cyclic shifts may include forward shifts as in FIG. 4B as well as backward shifts (e.g., stimulus 1 shifts to the position of stimulus E, and so forth), as well as any Nth shift (rather than merely one increment forward or backward); preferably N is relatively prime to M the number of stimuli in the sequence.

In one or more embodiments, the presentation of the sequence of control randomly generated stimuli 420 is determined by a set of predetermined rules designed to ensure the presentation of equivalent levels of difficulty across trials. Alternatively, prior user performance captured by the TVS 100 may be used to present a series of subsequent task versions 410 with increasing or decreasing levels of difficulty. For example, if a first task version 410 is characterized by the presentation of two stimuli and the subsequently captured user performance is greater than a threshold level, a subsequent task version 410 comprising three stimuli 420 may be presented to the user. In other embodiments, the TVS 100 may be configured to perform temporal cycling of stimulus presentation orders, inter-stimulus intervals or any combination thereof. For example, a stimulus 420 that was originally presented first in previously presented task version 410 may be presented last in a subsequent task version 430.

A task version generated from a prior task version based on a spatial relationships, such as task version 430 presented in FIG. 4B, may be evaluated by the task version generator 326 to determine that it conforms to any combination of following predetermined presentation rules, which are programmatically implemented in an algorithm executed by the task version generator 326:

Task versions comprising of five or fewer stimuli must not repeat stimuli.

No three consecutive stimuli in a task version may consist of numeric characters that constitute an ascending or descending sequence.

Any two sequential stimuli must be characterized by distinct alphanumeric characters.

In sequences comprising fewer than fifteen stimuli, no stimuli can appear more than twice.

A "1" or "0" cannot appear in a stimulus in the second position of a sequence of stimuli.

No sequence (including subsequence) of stimuli characterized by numeric characters forming a geometric sequence may appear. For example, the sequence (4, 8, 16) is geometric, whereas (4, 7, 16) is not.

No sequence (including subsequence) of stimuli characterized only by numeric characters forming an arithmetic sequence may appear. For example the sequence (1, 4, 7) is arithmetic, whereas (1, 4, 6) is not.

The first three stimuli comprising a task version must be distinct from the first three stimuli presented in the previously presented task version.

Between consecutively presented task versions no three sequence of stimuli may the same as those previously presented.

If a candidate task version fails the particular rules in effect, the task version generator 326 discards the candidate task version and generates another one.

The inter-stimulus interval (ISI) is the amount of time elapsed between the presentation of one stimulus and a next stimulus in a given task version. Moreover, ISIs may characterize the temporal relationships between two or more stimuli in a task version. In one or more embodiments, a second task version 430 may be generated by the task version generator module 326 to apply cyclic permutations of the ISIs characterizing a particular stimuli sequence. These task versions may enable the capture of user performance in terms of time, motion and distance in addition to user performance when presented with spatially varying task versions.

FIG. 4C illustrates a chart with an example of cyclic permutations of ISI for a task. The order column indicates the stimulus number for a stimulus in a sequence. The sequences columns (440A-440D) show four distinct stimuli sequences 1-4. Each stimuli sequence in turn comprises nine individual stimuli 420 presented in the listed order (i.e., 1 to 9) but with by the listed ISIs 460 associated with each individual stimulus. Thus, in sequence 1, the ISI between the first and second stimulus is 0.5 s 460, the ISI between the second and third stimulus is 0.5 s and so forth as indicted in the column 440A. In sequence 2, the ISIs have shifted, with the last ISI of 0.5 s 480 in column 440A being moved to the first position in sequence 2, depicted in column 440B, and all of the remaining ISIs shifted down (forward) in order. Similarly, for sequence 3 440C, the last ISI of 1 s from sequence 2 440B being moved to the first position in sequence 3 440C. A similar forward cyclic shift is used to create sequence 4 440D. These cyclic permutations produce unique equivalent task versions in accordance with an embodiment. Cyclic permutations may be applied to produce a number of stimuli sequences more or less than those illustrated herein. Additionally, in some embodiments, a stimulus sequence 440A, 440B. 440C, 440D may consist of a number of distinct stimuli more or less than the number of stimuli associated with a given stimuli sequence illustrated in accordance with FIG. 4C.

In other embodiments, stimuli within a specific stimuli sequence are presented at defined ISIs. The sequence of stimuli is characterized by the number of stimuli repetitions, the number of inter stimuli shifts, and increasing or decreasing ISI. TVS 100 may track the ISIs associated with previously administered stimuli sequences to ensure that subsequently presented stimuli sequences are unique.

FIG. 5 illustrates possible second task versions generated by TVS 100 for a task type. The second task versions preserve relative inter and intra stimulus relationships (e.g., distances and angles) from a first task version based on a task type stored in the task store 330. Second task versions may be generated from a previously presented first task type by applying a symmetric geometric transformation comprising either a rotation or reflection in accordance with an embodiment.

Figure 5A:
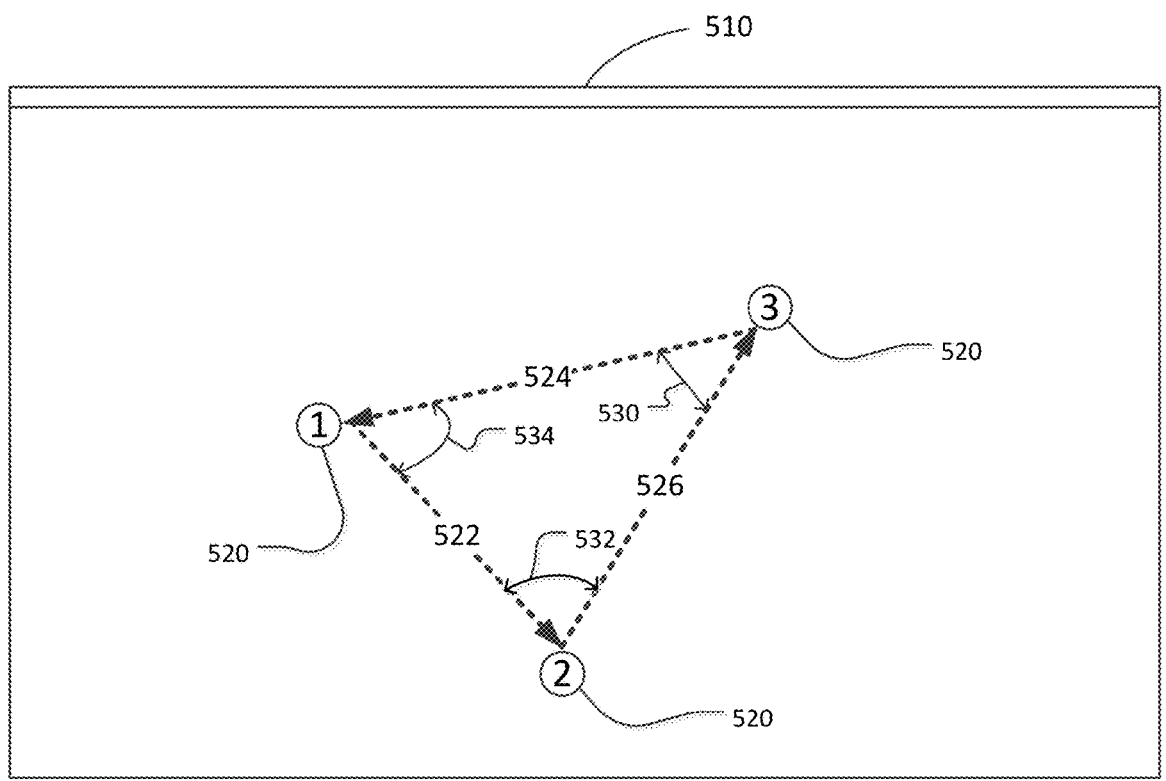

FIG. 5A depicts a first task version 510 associated with a task type comprising a sequence of three stimuli 520 wherein the stimuli locations are arranged in a fixed position on the client device 120, here forming a triangle. The presented stimuli 520 are characterized with numeric symbols "1", "2" and "3". The three stimuli are separated from one another by relative distances 524, 526 and 522 and angles 532, 534 and 534. The task type requires the user to draw lines on the client device 120 connecting the stimulus symbols in the sequence from 1 to 3 and back to 1. Here too, if the user was presented this task multiple times shown in FIG. 5A, they would quickly learn the pattern and improve their performance with each subsequent presentation of the task.

Figure 5B:
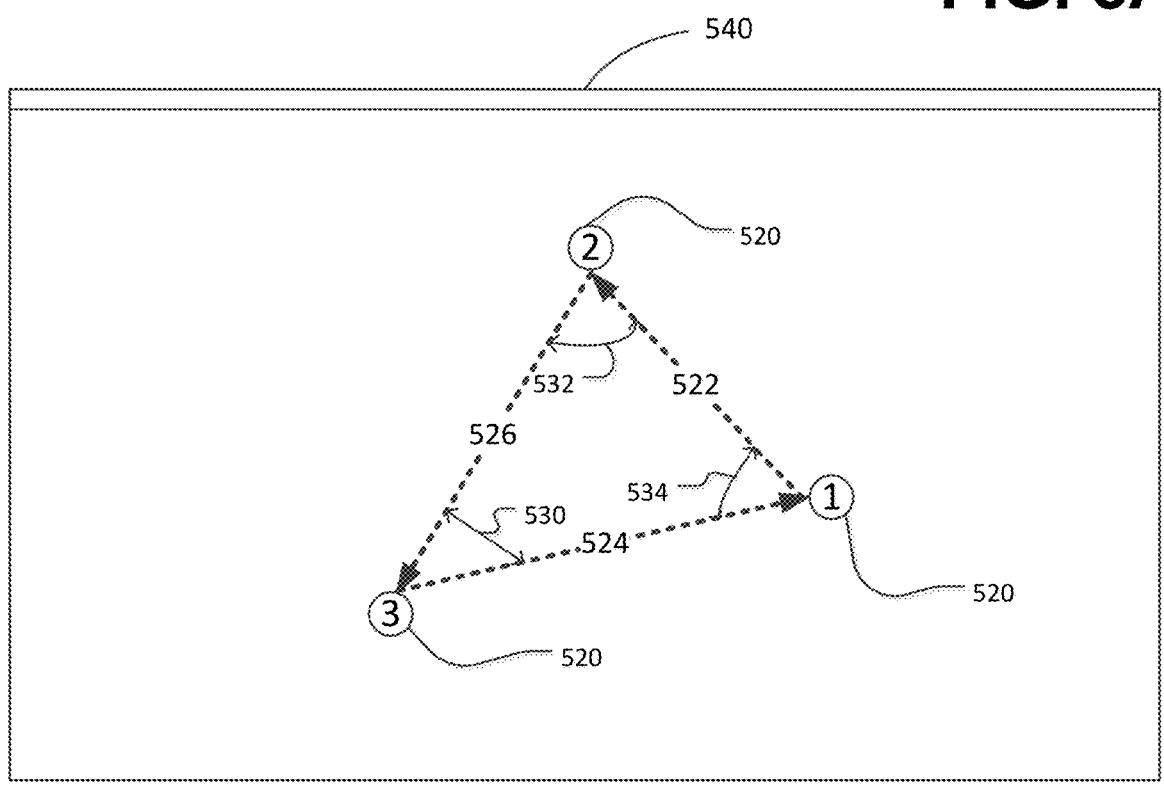

FIG. 5B illustrates a unique, equivalent second task version 540 generated by the task version generator 326 based on the first task version 510. That is, task version 540 contains the same number of stimuli and substantially preserves the spatiotemporal relationships originally presented in accordance with the first task version 510.

The task version depicted in FIG. 5B is a second task version of the previously presented task type comprising a stimuli sequence generated by performing a graphical transformation. The graphical transformation may be a geometric rotation of a hundred and eighty degrees (180°) on the stimuli sequence delineated in FIG. 5A, where the triangle formed by the stimuli is rotated about a central point (not shown). The rotation illustrated in FIG. 5B preserves relative angles 530, 532, 534, and distances 522, 524, 526. In one or more embodiments, individual stimuli within a sequence of stimuli can be graphically rotated or reflected in addition to rotations and reflections of stimuli sequences. In some embodiments, TVS 100 may be configured to track the starting point of the stimuli sequence in terms of the center of the presented stimuli sequence and/or the base of individual stimuli comprising the presented stimuli sequence. Additionally, in other embodiments, TVS 100 may be configured to also track inter and intra stimuli sequence temporal relationships. The captured spatiotemporal relationships in the may be cycled and the spatial relationship of the presented sequence of stimuli to produce unique equivalent task versions 540.

Figure 5C:
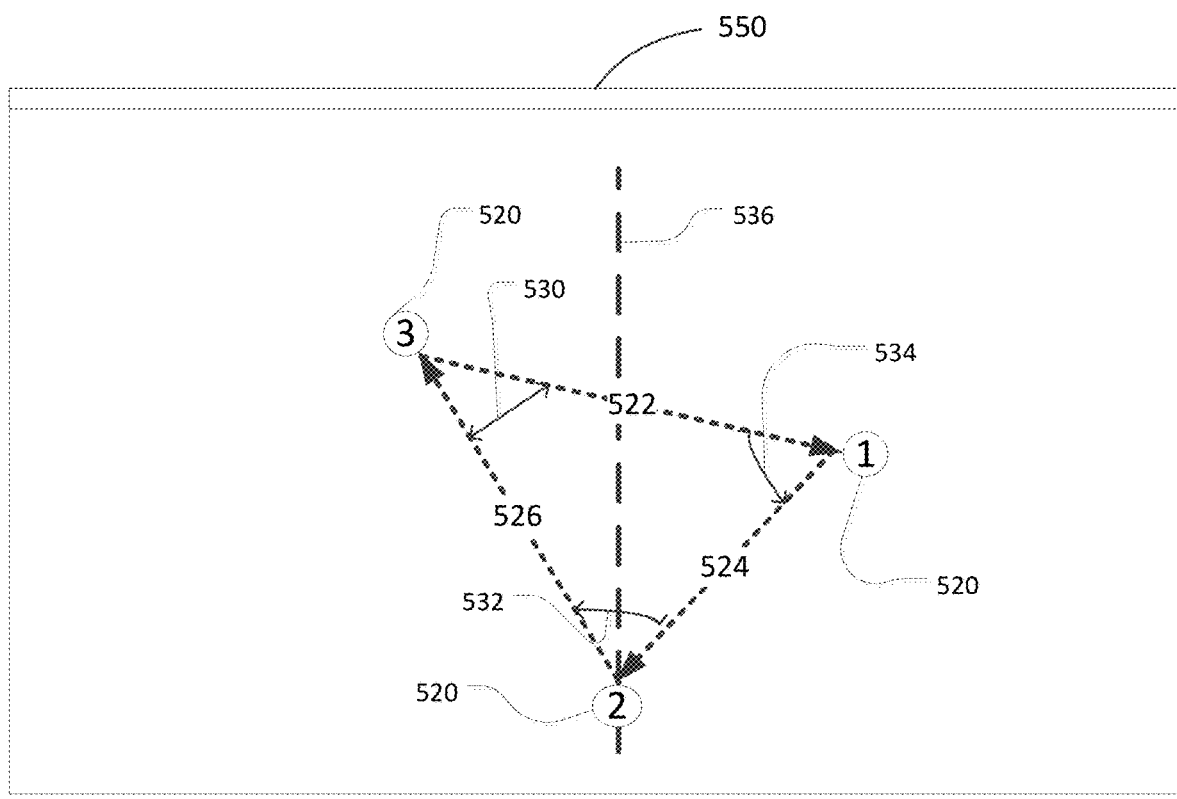
Figure 5D:
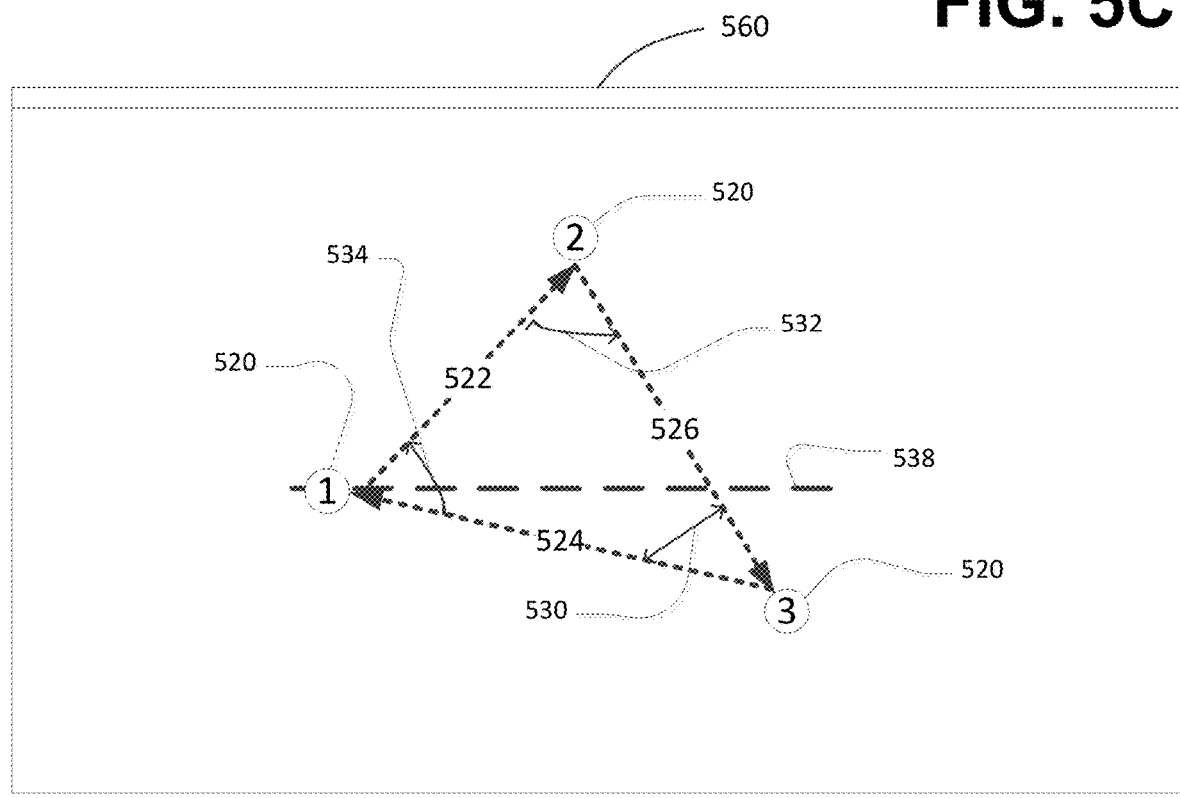

FIG. 5C illustrates an unique equivalent second task version comprising a stimuli sequence of three stimuli 520 generated by performing a graphical transformation comprising a reflection of the stimuli sequence depicted in the first task version 510 about a vertical axis. The reflection illustrated in FIG. 5C is performed across axis 536 and preserves angles 530, 532, 534, and distances 522, 524, 526, between adjacent stimuli 520. Similarly, FIG. 5D illustrates a possible second unique equivalent task version 550. Task version 550 depicts a stimuli sequence containing three stimuli 520 generated by performing a graphical transformation comprising a reflection of the stimuli sequence delineated in a first task version 510 about a horizontal axis. The reflection illustrated in FIG. 5D is performed across axis 538 and preserves angles 530, 532, 534, and distances 522, 524, 526, between adjacent stimuli 520. Reflections about a common axis of symmetry (e.g., horizontal or vertical axis) allow the conversion of an originally L stimulus to an R stimulus and vice versa.

FIG. 5E illustrates a chart with an example of cyclic permutations of ISI for a task coupled with geometric symmetry transformation resulting in L or R stimuli. The order column 590 indicates the stimulus presentation order for a stimulus 520 in stimulus sequence 570A-D. Each stimuli sequence, in turn, comprises nine individual stimuli 520 presented in the listed order (i.e., 1 to 9) but with the listed ISI 586, 588 and sidedness 582 and 584 associated each individual stimulus. FIG. 5E shows that in sequence 1, the ISI between the first and second stimulus is 0.5 s 586 and the sidedness of the first stimulus is L 586. The ISI between the second and third stimulus is also 0.5 s and the second stimulus has sidedness L and an ISI of 0.5 s and so forth as indicated in sequence 1 570A. In sequence 2 570B, the ISIs and sidedness of the stimuli have shifted such that the last of the sidedness and ISI in sequence 1, 584 and 588 respectively, is moved to the first position in sequence 2 570B and the sidedness of all the stimuli comprising sequence 2 570B have been flipped (e.g., a stimulus that L in sequence 1 570A is R in sequence 2 570B). All of the remaining ISI and sidedness are shifted down (forward). A similar forward cyclic shift is used to create sequence 3 in column 570C where the last ICI and sidedness from sequence 2 440B is moved to the first position in sequence 3. Similarly, for sequence 3 (column 3 440C), the last ISI of 1 s from column 2 440B being moved to the first position in sequence 440C. A similar forward cxyclic shift is used to create sequence 4, 570D.

Transformations that are temporal cyclic permutations produce unique equivalent task versions. In one or embodiments, transformations that are both temporal cyclic permutations and geometric transformations comprising reflections and/or rotations may be applied to produce a number of stimuli comprising additional unique equivalent task versions associated with a task type. In other embodiments, transformations may also include positional cyclic permutations. For example, a stimuli sequence comprising a first stimulus and a second stimulus during a first task version may be cycled such that the second stimulus is presented in place of the first and the first stimulus takes the place of the second in a subsequent task version In still other embodiments, equivalent unique task versions may be generated by cycling geometric properties alone. For example, a stimuli or a group of stimuli comprising a stimuli sequence may be reflected, rotated or any combination thereof.

Additionally, in some embodiments, a stimulus sequence 570A, 5700B. 570C and 570D may comprise a number of distinct stimuli more or less than the number of stimuli associated with a given stimuli sequence illustrated in accordance with FIG. 5E. The TVS 100 may also create a task version 540 based on prior user performance. The TVS 100 may generate a second task version 540, 550 or 560 comprising a different number of stimuli 520 than the number of stimuli 520 presented in previously displayed task version 510.

Figure 6A:
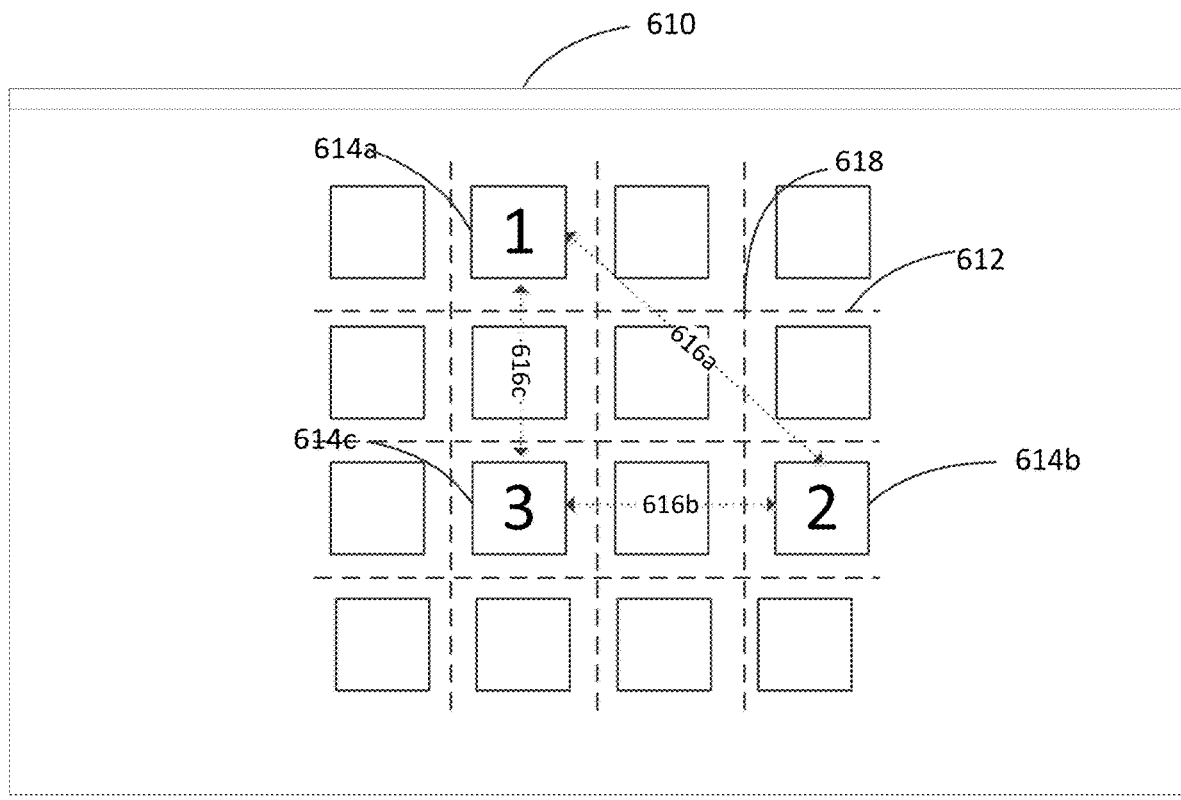
FIGS. 6A-C illustrate an embodiment of a task version configured to enable the measure of the spatial span of a stimuli sequence in accordance with an embodiment.

FIG. 6A illustrates an embodiment of a first task version 610 associated with a task type configured to measure motor skills. FIG. 6A illustrates a first task version 610 displayed on a client device 120 comprising three stimuli 614a-c labeled by alpha numeric symbols separated by a grid 612 not visible on a client device 120 but used for spacing and interaction purposes. Task version 610 may be associated with a task type comprising a stimuli sequence of eight stimuli of which three contain numeric symbols "1" 614a, "2" 614b and "3" 614c and are arranged to form a triangle. Specifically, the three stimuli 614a-c are arranged to form an isosceles right triangle such that the legs of the isosceles triangle define the spatial relationship between two stimuli. Thus the stimuli are separated from each other by defined distances 616a-c and 620. The associated task type may require the user to trace the path between stimuli 614 on the client device 120 in an ascending or descending manner. For example, the user may be prompted by the TVS 100 to trace the path from"1" 614a to "2" 614b, 2 614b to 3 614c and back to 1 614a. Here too, if the user was presented this task multiple times shown in FIG. 6A, they would quickly learn the pattern and improve their performance with each subsequent presentation of the task.

Figure 6B:
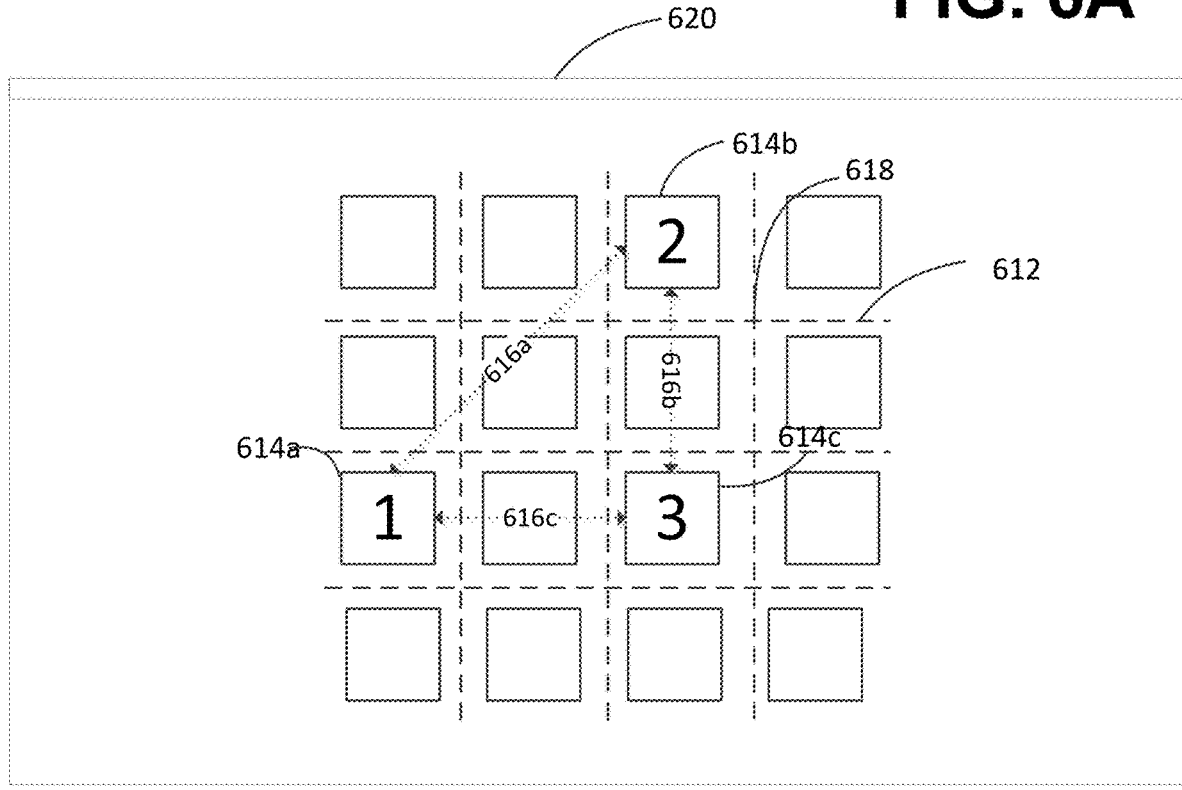

FIG. 6B illustrates a second task version 620 generated by task version generator module 326 by performing one or more spatial and symmetric transformations on the stimuli sequence associated with the first task version 610. Task version 620 depicts substantially the same stimuli sequence presented in task version 610 after a rotation of ninety degrees (90°) about stimulus 614c followed by a translation of one grid point 618 to the right. Once again the user may be required to trace the path between stimuli in ascending or descending manner but the user's start and end points have been changed while the difficulty of the task version 620 is effectively the same as that of task version 610.

Figure 6C:
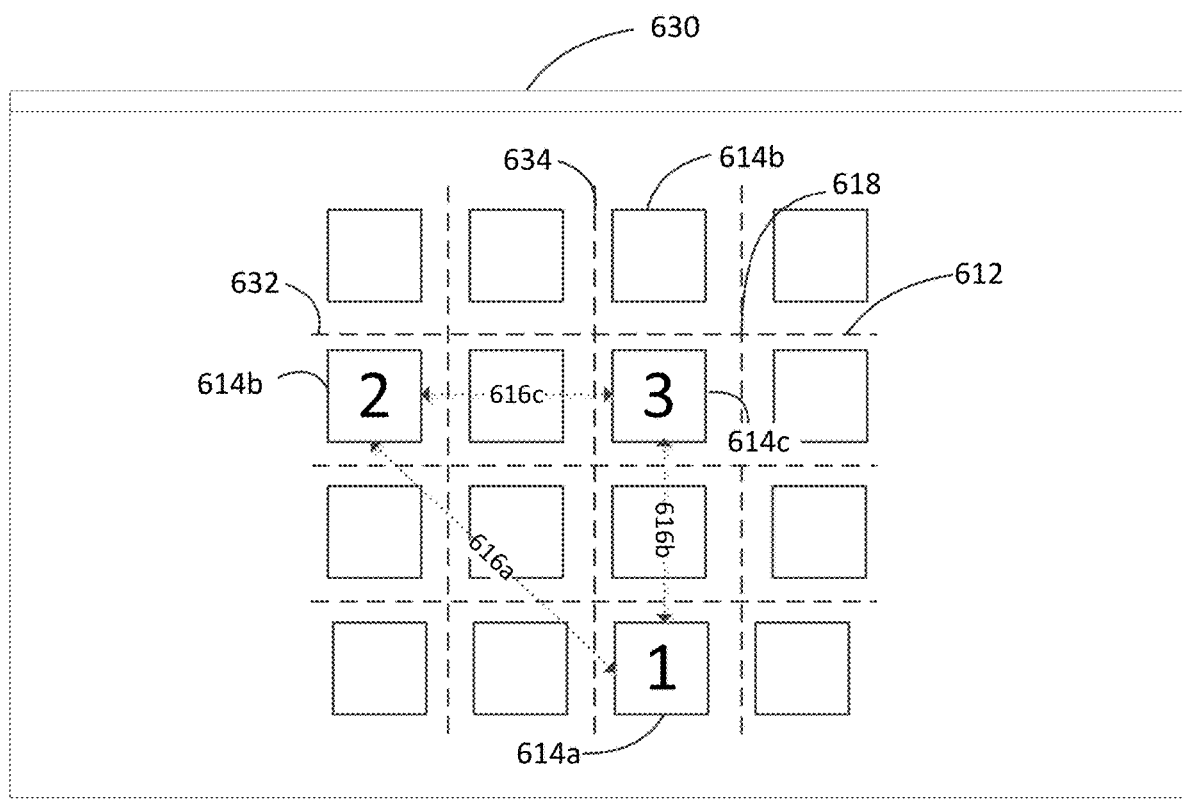

FIG. 6C illustrates a second task version 630 generated by task version generator module 326 by performing one or more spatial and symmetric transformations on the stimuli sequence associated with the first task version 610. FIG. 6C also contains horizontal axis 632 and vertical axis 634 which are part of the invisible grid 612. Task version 630 depicts substantially the same stimuli sequence presented in task version 610 after a rotation of a hundred and eighty degrees (180°) about stimulus 614c followed by a horizontal translation of one grid point 618 to the right. Alternatively, the stimuli sequence of task version 630 can be obtained from that of task version 610 by performing a reflection across horizontal axis 632 followed by a vertical reflection across horizontal axis 634 and finally a horizontal translation of 1 grid point 618 to the right.

In some embodiments, transformations may comprise cyclic permutations of spatial relationships between one or more stimuli in a stimuli sequence. These spatial relationships may be vertical or horizontal translations, rotations, reflections or any combination of transformations that preserve angle and distance relationships between adjacent stimuli. In other embodiments, task version 610 may comprise a stimuli sequence comprising of a number of stimuli more or less than three.

In some embodiments the TVS 100 may generate unique equivalent task versions by permutating the symmetric and spatial properties of one or more stimuli in a sequence of stimuli. That is, the arrangement of objects can shift location along the lateral or vertical axis, be reflected along the lateral or vertical axis, or be manipulated through orientation and positional shifts to preserve angle and distance measurements. In one or more embodiments, the TVS 100 may be configured to track and manipulate geometric and/or spatial relationships (distance and position) between adjacent stimuli in a across and in between different unique equivalent task versions.

Figure 7:
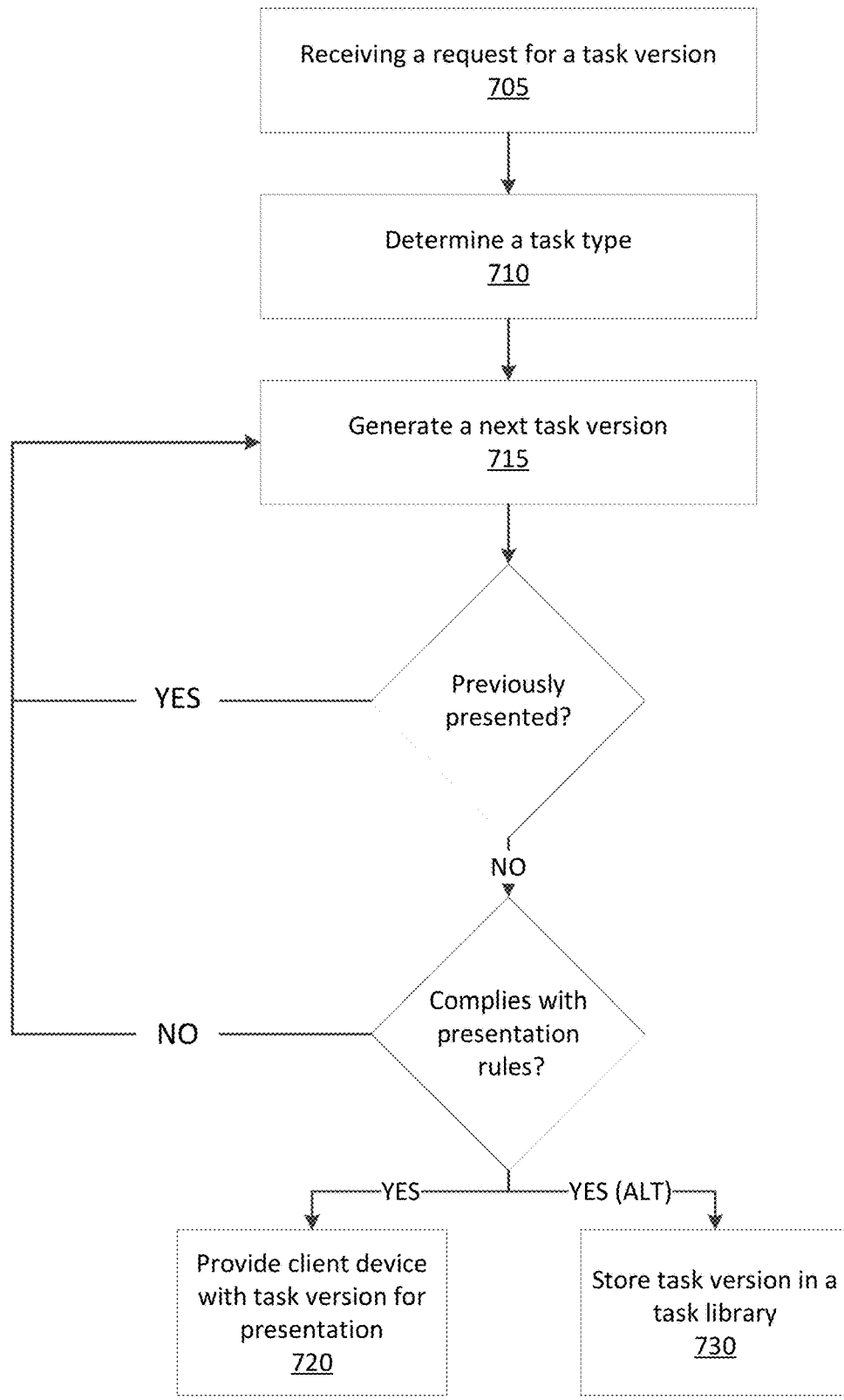
FIG. 7 is a flow chart of a process for generating task versions.

FIG. 7 illustrates an embodiment of a generation process for a task version associated with a task type to be presented on the client device 120. In the illustrated task version selection process, task versions are selected based on the user's previous performance, a set of predetermined presentation and interaction rules associated with a particular task type. In this embodiment, TVS 100 receives a request for a task version 705 including data associated with the user. The data associated with the user may include, completed task types and task versions, a measure of the user's prior performance and previously presented task versions. This user information is then used to determine a task type 710 to be presented from a set of predetermined set of task types in the task type store 330.

In this embodiment, generating a next task version 715 may involve performing a plurality of predetermined geometric transformations on one or more stimuli comprising the stimuli sequence of a previously presented task version associated with the determined task type 710. The, geometric transformations may include cyclic permutations of symmetric properties such as rotation or reflection about a local stimulus axis while maintaining inter and intra stimulus spatial relationships, a cyclic permutations of stimuli positional properties resulting in a graphical translation, cyclic permutations of presentation times or any combination thereof.

The generated next task version is checked against previous user data such as previously presented task versions associated with the determined task type 710. For example, each the spatiotemporal relationships of a stimulus in the next task version is checked against the spatiotemporal relationships of one or more stimuli comprising a previously presented task version associated with the determined task type that has been completed by the user. In one or more embodiments, the generated task version may also be checked against a set of predetermined presentation rules, such as those listed above, associated with determined task type. If the task version fails any of these checks it is discarded a new task version is generated 715 based on the received request for a task version 705 and the determined task type 710. In this way TVS 100 ensures that the generated task version is unique and equivalent.

In one or more embodiments, the task versions associated with a particular task type determined to be unique and equivalent through the process flow illustrated in FIG. 7 may be provided to client device 120 for presentation 720. Alternatively, TVS 100 may store the generated unique, equivalent task version associated with a particular task type in a task library 730 for presentation to client device 120 at a later time. In one or more embodiments, this task library is maintained in task store 330.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

The invention claimed is:

1. A computer implemented method comprising:
receiving, at a client device comprising a processor and memory and capable of receiving input from a first user, a first data associated with the first user identifying which versions of a computer-mediated task type have been previously completed by the first user, each version of the computer-mediated task type comprising a computer-based presentation of a grouping of two or more stimuli included in a virtual plane on the client device, wherein the first user provides inputs to the client device with respect to a stimulus to complete the version of the computer-mediated task type;
determining, at the client device, a computer-mediated task type from one or more previously completed versions of the computer-mediated task types by the first user;
generating, at the client device, a next version of the computer-mediated task type to be presented to the first user, by applying at least one transformation associated with the determined computer-mediated task type to the virtual plane including the two or more stimuli in a version of the computer-mediated task type previously completed by the first user, wherein each transformation comprises:
a graphical reflection of the virtual plane around a single axis, wherein the virtual plane includes the grouping of the two or more stimuli, wherein the graphical reflection of the virtual plane is one of a plurality of graphical reflections of the virtual plane, and wherein an order of the plurality of graphical reflections is prescribed by multiple sequences of graphical reflections, and wherein the multiple sequences of graphical reflections include reflecting the virtual plane around the single axis multiple times with different axis locations in each graphical reflection, and wherein a first sequence of graphical reflections of the multiple sequences of graphical reflections repeats an order of a location of the single axis included in a second sequence of the plurality of graphical reflections;
determining, at the client device, whether each stimulus included in the transformed virtual plane in the next version of the computer-mediated task type satisfies a predetermined plurality of spatial, temporal and alphanumeric relationships with respect to an adjacent stimulus in the sequence;
determining, at the client device, whether each stimulus included in the transformed virtual plane in the next version of the computer-mediated task type has been previously presented;
responsive to determining that each stimulus in the next version of the computer-mediated task type does not satisfy the predetermined plurality of spatial, temporal and alphanumeric relationships, repeating, at the client device, the generating of a next version of the task;
responsive to determining whether each stimulus included in the transformed virtual plane in the next version of the computer-mediated task type has been previously presented, repeating, at the client device, the generating of a next version of the task; and
presenting, at the client device, the generated task including the transformed virtual plane in the computer-mediated task on the client device, wherein each task requires a response to one or more stimuli in the grouping of two or more stimuli included in the transformed virtual plane.

2. The method of claim 1, wherein of the computer-mediated task type further comprises:
receiving, at the client device, a unique ID of the next version of the computer-mediated task type wherein version of the computer-mediated task type data is referenced by a user id; and
responsive to a prior progress of the first user, generating, at the client device, the grouping of two or more stimuli, wherein the computer-mediated task type data indicates a sequence of stimuli and attributes of each stimulus in the grouping of two or more stimuli.

3. The method of claim 1, wherein generating the next version of the computer-mediated task type further comprises:
responsive to inter-stimulus temporal relationships of the grouping of two or more stimuli in a previously presented version of the computer-mediated task type, wherein each inter-stimulus temporal relationship comprises one of the set of temporal relationships consisting of: presentation order, presentation time, presentation interval, generating, at the client device, the next version of the computer-mediated task type by performing a temporal transformation comprising of a cyclic permutation on the temporal presentation order in the previously presented version of the computer-mediated task type.

4. The method of claim 1, wherein generating the next version of the computer-mediated task type further comprises:
responsive to cyclic permutations of spatial location of the grouping of two or more stimuli in a previously completed version of the task, wherein the stimulus spatial location comprises an x location and a y location, generating, at the client device, the next version of the computer-mediated task type by performing a graphical transformation comprising of the spatial relationship between two or more stimuli in a previously presented version of the computer-mediated task type.

5. The method of claim 4, wherein generating the next version of the computer-mediated task type further comprises:
maintaining, at the client device, relative distance the two or more stimuli included in the previously presented version of the computer-mediated task type.

6. The method of claim 4, wherein generating the next version of the computer-mediated task type further comprises:
maintaining, at the client device, relative distance and angles with reflection between the two or more stimuli included in the previously presented version of the computer-mediated task type.

7. The method of claim 4, wherein generating the next version of the computer-mediated task type further comprises:
maintaining, at the client device, relative distance and angles with rotation between the two or more stimuli included in the previously presented version of the computer-mediated task type.

8. The method of claim 4, wherein generating the next version of the computer-mediated task type further comprises:
maintaining, at the client device, relative distance and angles with reflection and rotation between the two or more stimuli included in the previously presented version of the computer-mediated task type.

9. A system comprising:
a processor; and
a non-transitory computer-readable medium comprising instructions that when executed by the processor cause the processor to:
receive a first data associated with a first user identifying which versions of a computer-mediated task type have been previously completed by the first user, each version of the computer-mediated task type comprising a computer-based presentation of a grouping of two or more stimuli included in a virtual plane or more stimuli on a client device, wherein the first user provides inputs to the client device with respect to a stimulus to complete the version of the computer-mediated task type;
determine a computer-mediated task type from one or more previously completed versions of the computer-mediated task types by the first user;
generate a next version of the computer-mediated task type to be presented to the first user, by applying at least one transformation associated with the determined computer-mediated task type to the virtual plane including the two or more stimuli in a version of the computer-mediated task type previously completed by the first user, wherein each transformation comprises:
a graphical reflection of the virtual plane around a single axis, wherein the virtual plane includes the grouping of the two or more stimuli, wherein the graphical reflection of the virtual plane is one of a plurality of graphical reflections of the virtual plane, and wherein an order of the plurality of graphical reflections is prescribed by multiple sequences of graphical reflections, and wherein the multiple sequences of graphical reflections include reflecting the virtual plane around the single axis multiple times with different axis locations in each graphical reflection, and wherein a first sequence of graphical reflections of the multiple sequences of graphical reflections repeats an order of a location of the single axis included in a second sequence of the plurality of graphical reflections;
determine whether each stimulus included in the transformed virtual plane in the next version of the computer-mediated task type satisfies a predetermined plurality of spatial, temporal and alphanumeric relationships with respect to an adjacent stimulus in the sequence;
determine whether each stimulus included in the transformed virtual plane in the next version of the computer-mediated task type has been previously presented;
respond to determining that each stimulus in the next version of the computer-mediated task type does not satisfy the predetermined plurality of spatial, temporal and alphanumeric relationships, repeating the generating of a next version of the task;
respond to determining whether each stimulus included in the transformed virtual plane in the next version of the computer-mediated task type has been previously presented, repeating the generating of a next version of the task; and
present the generated task including the transformed virtual plane in the computer-mediated task on the client device, wherein each task requires a response to one or more stimuli in the grouping of two or more stimuli included in the transformed virtual plane.

10. The system of claim 9, wherein the instructions for generating the next version of the computer-mediated task type further cause the processor to:
receive a unique ID of the next version of the computer-mediated task type wherein version of the computer-mediated task type data is referenced by a user id;
respond to a prior progress of the first user;
generate the grouping of two or more stimuli, wherein the computer-mediated task type data indicates a sequence of stimuli and attributes of each stimulus in the grouping of two or more stimuli.

11. The system of claim 9, wherein the instructions for generating the next version of the computer-mediated task type further causes the processor to:
respond to inter-stimulus temporal relationships of the grouping of two or more stimuli in a previously presented version of the computer-mediated task type, wherein each inter-stimulus temporal relationship comprises one of the set of temporal relationships consisting of: presentation order, presentation time, presentation interval; and
generate the next version of the computer-mediated task type by performing a temporal transformation comprising of a cyclic permutation on the temporal presentation order in the previously presented version of the computer-mediated task type.

12. The system of claim 9, wherein the instructions for generating the next version of the computer-mediated task type further cause the processor to:
responsive to cyclic permutations of spatial location of the grouping of two or more stimuli in a previously completed version of the task, wherein the stimulus spatial location comprises an x location and a y location; and
generating the next version of the computer-mediated task type by performing a graphical transformation comprising of the spatial relationship between two or more stimuli in a previously presented version of the computer-mediated task type.

13. The system of claim 12, wherein the instructions to generate the next version of the computer-mediated task type further cause the processor to:
maintain relative distance between the two or more stimuli included in the previously presented version of the computer-mediated task type.

14. The system of claim 12, wherein the instructions for generating the next version of the computer-mediated task type further cause the processor to:
maintain relative distance and angles with reflection between the two or more stimuli included in the previously presented version of the computer-mediated task type.

15. The system of claim 12, wherein the instructions for generating the next version of the computer-mediated task type further causes the processor to:
maintain relative distance and angles with rotation between the two or more stimuli included in the previously presented version of the computer-mediated task type.

16. The system of claim 12, wherein the instructions for generating the next version of the computer-mediated task type further causes the processor to:

maintain relative distance and angles with reflection and rotation between the two or more stimuli included in the previously presented version of the computer-mediated task type.

* * * * *